(12) United States Patent
Rashid et al.

(10) Patent No.: US 12,259,375 B2
(45) Date of Patent: Mar. 25, 2025

(54) METHOD AND APPARATUS FOR METHANE MANAGEMENT

(71) Applicant: Cameron International Corporation, Houston, TX (US)

(72) Inventors: Kashif Rashid, Cambridge, MA (US); Lukasz Zielinski, Cambridge, MA (US); Andrew J. Speck, Cambridge, MA (US)

(73) Assignee: CAMERON INTERNATIONAL CORPORATION, Houston, TX (US)

( * ) Notice: Subject to any disclaimer, the term of this patent is extended or adjusted under 35 U.S.C. 154(b) by 0 days.

(21) Appl. No.: 18/704,256

(22) PCT Filed: Dec. 8, 2022

(86) PCT No.: PCT/US2022/081142
§ 371 (c)(1),
(2) Date: Apr. 24, 2024

(87) PCT Pub. No.: WO2023/108041
PCT Pub. Date: Jun. 15, 2023

(65) Prior Publication Data
US 2024/0418693 A1 Dec. 19, 2024

Related U.S. Application Data

(60) Provisional application No. 63/265,122, filed on Dec. 8, 2021.

(51) Int. Cl.
*G01M 3/16* (2006.01)
*G01N 33/00* (2006.01)
(Continued)

(52) U.S. Cl.
CPC .......... *G01N 33/0075* (2013.01); *G01M 3/16* (2013.01); *G01W 1/10* (2013.01); *G06F 30/28* (2020.01)

(58) Field of Classification Search
CPC .......................... G01N 33/0075; G01W 1/02
See application file for complete search history.

(56) References Cited

U.S. PATENT DOCUMENTS 9,322,735 B1 * 4/2016 Tan .................. G01W 1/00
11,454,622 B2   9/2022 Billat
(Continued)

FOREIGN PATENT DOCUMENTS

KR    20150138941 A    12/2015
KR    20160008781 A     1/2016
(Continued)

OTHER PUBLICATIONS

Kemp et al., 2021, New Technologiescan Cost-effectively Reduce Oil and 1Gas Methane Emissions, but Policieswill Require Careful2Design to Establish Mitigation Equivalence, published Jan. 22, 2021, non-peer reviewed pre-print submitted to EarthArXiv, downloaded from https://eartharxiv.org/repository/view/2008/ (40 pages).

(Continued)

*Primary Examiner* — Hongmin Fan
(74) *Attorney, Agent, or Firm* — Jeffrey D. Frantz

(57) ABSTRACT

Systems and methods presented herein generally relate to greenhouse gas emission management and, more particularly, to a greenhouse gas emission management workflow to perform greenhouse gas detection sensor placement or greenhouse gas leak detection. For example, the system and method enable improved gas sensor arrangements within an oil and gas worksite. In another example, the system and method enable the prediction of a location and a leak rate of a gas leak within an oil and gas production facility based on measurements collected by gas leak sensors disposed within the facility and prevailing wind information.

13 Claims, 12 Drawing Sheets

(51) Int. Cl.
*G01W 1/10* (2006.01)
*G06F 30/28* (2020.01)

(56) References Cited

U.S. PATENT DOCUMENTS

| | | |
|---|---|---|
| 2009/0287520 A1 | 11/2009 | Zimmerman |
| 2010/0198736 A1 | 8/2010 | Marino |
| 2011/0040493 A1 | 2/2011 | Choi |
| 2012/0010917 A1 | 1/2012 | De Godoi |
| 2013/0246027 A1 | 9/2013 | Rodriguez |
| 2014/0081579 A1 | 3/2014 | Tyburski |
| 2015/0185194 A1 | 7/2015 | Prince et al. |
| 2017/0003684 A1 | 1/2017 | Knudsen |
| 2017/0097274 A1 | 4/2017 | Thorpe et al. |
| 2017/0147958 A1 | 5/2017 | Hatfield |
| 2018/0266240 A1 | 9/2018 | Jaaskelainen |
| 2018/0266241 A1 | 9/2018 | Ferguson |
| 2018/0292374 A1 | 10/2018 | Dittberner |
| 2019/0285600 A1 | 9/2019 | Klein et al. |
| 2019/0366400 A1 | 12/2019 | Chambers |
| 2019/0386790 A1 | 12/2019 | Hawinkel |
| 2020/0240259 A1 | 7/2020 | Balasubramaniam |
| 2020/0371079 A1 | 11/2020 | Abedini |
| 2022/0008972 A1 | 1/2022 | Quigley |
| 2022/0065834 A1 | 3/2022 | Gadot |
| 2023/0176023 A1 | 6/2023 | Wang |

FOREIGN PATENT DOCUMENTS

| | | |
|---|---|---|
| KR | 2020-0074648 A | 6/2020 |
| WO | 2016089979 A1 | 6/2016 |
| WO | 2023033832 A1 | 3/2023 |

OTHER PUBLICATIONS

RSG, What is Responsibly Sourced Gas, https://www.projectcanary.com/responsibly-sourced-gas/, downloaded on Sep. 3, 2021, copyright 2021 (5 pages).
International Search Report and Written Opinion of PCT Application No. PCT/US2021/048981 dated Dec. 23, 2021, 10 pages.
International Search Report and Written Opinion of PCT Application No. PCT/US2021/048977 dated Jun. 3, 2022 9 pages.
Alvarez, et al. "Assessment of methane emissions from the US oil and gas supply chain." Science 361.6398 (2018): 186-188.
Stockie, John M. "The mathematics of atmospheric dispersion modeling." Siam Review 53.2 (2011): 349-372.
Briggs, G. A. "Optimum formulas for buoyant plume rise." Philosophical Transactions of the Royal Society of London. Series A, Mathematical and Physical Sciences 265.1161 (1969): 197-203.
Hanna et al., Handbook on atmospheric diffusion. No. DOE/TIC-11223. National Oceanic and Atmospheric Administration, Oak Ridge, TN (USA). Atmospheric Turbulence and Diffusion Lab., 1982.
EPA ISC3 method, https://www.epa.gov/scram/air-quality-dispersion-modeling-alternative-models#isc3 (16 pages).
EPA OTM33a method, https://www.epa.gov/emc/emc-other-test-methods#Other%20Test%20Methods (20 pages).
Fugitive Emissions Abatement Simulation Testbed (FEAST) software, https://github.com/EAOgroup/FEAST (6 pages).
Seinfeld et al., Atmospheric chemistry and physics: from air pollution to climate change. John Wiley Sons, 2016, Sections 18.10-18.11, pp. 859-868.
Turner, D. Bruce. Workbook of atmospheric dispersion estimates: an introduction to dispersion modeling. CRC press, 1994, Sections 2.4-2.9, pp. 2-3 to 2-13.
De Visscher, Alex. Air dispersion modeling: foundations and applications. John Wiley Sons, 2013, sections 6.3-6.5, pp. 145-152.
Ponish, A., et al, "Some guidelines for genetic algorithm implementation in MINLP batch plant design", Advances in Metaheuristics for Hard Optimization: p. 293., Springer, 2007.
Whitley, D., "Next generation genetic algorithms: A users guide", Handbook of Metaheuristics, Springer, 2019, p. 245-274.
PCT International Search Report and Written Opinion; Application No. PCT/US2022/081142; Dated Apr. 25, 2023; 12 pages.

* cited by examiner

METHOD AND APPARATUS FOR METHANE MANAGEMENT

CROSS REFERENCE TO RELATED APPLICATION

This application is a National Stage Entry of International Application No. PCT/US2022/081142, filed Dec. 8, 2022, which claims priority from and the benefit of U.S. Provisional Application Ser. No. 63/265,122, entitled "Method and Apparatus for Methane Management", filed Dec. 8, 2021, which is hereby incorporated by reference in its entirety.

BACKGROUND

The present disclosure generally relates to greenhouse gas emission monitoring and, more particularly, to a method and apparatus to perform methane leakage management, including gas sensor placement and/or methane leak detection for oil and gas production facilities.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as an admission of any kind.

Methane is a relatively potent greenhouse gas and the main component of natural gas. The process of extracting and processing natural gas inevitably results in some methane emissions, and those emissions lead to global warming, contributing significantly to climate change. As such, operators in upstream/midstream oil and gas are interested in reducing methane emissions from their facilities. Such emissions arise from a range of facilities (e.g., single wells to gas plant), sources (e.g., intentional vents to unintentional fugitive leaks), and equipment (e.g., tanks, compressors, separators, pneumatic controllers, and so forth). Thus, methane emissions can be reduced by a variety of technologies including leak detection, leak repair, venting elimination, and data management. Indeed, hardware technologies for fugitive leak monitoring include optical gas imaging (OGI), sensor measurement, and some recent novel techniques. Optical gas imaging (OGI) is a thermal imaging technology using high-sensitivity infrared cameras to detect fugitive gas emissions and has become the detection method recommended by the Environmental Protection Agency (EPA). OGI camera performance may depend on emission rates, environmental conditions, and other factors, such as the design, adjustment, and use protocols of the system. Gas sensors are devices that measure the concentration of a certain gas in one single location placed near the leak location. Some recent novel techniques may include unmanned inspection of facilities using robots or drones or the like. This may reduce labor cost in the long term and may present advantage for scenarios that are difficult to monitor (DTM) or unsafe to monitor (UTM).

There are many sensor, cameras, and novel technologies in the commercial market, and each may have advantages and disadvantages in terms of detection range, accuracy, and cost. However, on top of the hardware technologies, sensor placement planning remains an unsolved problem. In order to monitor gas leakage across a large area or an entire facility, simply installing the gas sensors without any plan to optimize the sensor deployment will result in excessive capital cost expenditure, while providing no assurance that the deployment will provide desired results or returns. While a site survey may be useful in planning sensor deployment, it is expensive and not easy to carry out, especially since multiple factors cannot be determined using a single site survey, such as wind condition (which varies constantly) and current gas leakage status.

There is a need to provide a systematic solution, based on numerical modeling, to plan the location of greenhouse gas leakage detection sensors in an optimal way, such that the plan covers as many potential leak sources in a facility as possible while maintaining economic budget.

SUMMARY

A summary of certain embodiments described herein is set forth below. It should be understood that these aspects are presented merely to provide the reader with a brief summary of these certain embodiments and that these aspects are not intended to limit the scope of this disclosure.

In an embodiment, a greenhouse gas emission analysis (GGEA) system includes at least one memory configured to store a plume model, and at least one processor configured to execute stored instructions to perform actions. The actions include receiving gas concentration measurements from gas sensors communicatively coupled to the GGEA system and receiving wind measurements from wind sensors communicatively coupled to the GGEA system. The actions include convolving the gas concentration measurements and the wind measurements into valid event records and predicting a location and leak rate of a gas leak within a worksite based at least in part on the valid event records and the plume model.

In an embodiment, a method of predicting a location and leak rate of a gas leak within a worksite includes receiving gas concentration measurements from gas sensors disposed within the worksite and receiving wind measurements from wind sensors disposed within the worksite. The method includes convolving the gas concentration measurements and the wind measurements into valid event records and predicting a location and leak rate of a gas leak within the worksite based at least in part on the valid event records and a plume model.

In an embodiment, a method includes using historical weather data to generate a stochastic wind model for the worksite over a forecast time period of interest and discretizing the stochastic wind model into time periods to generate a wind schedule, wherein each time period of the wind schedule includes at least a wind speed and a wind direction. The method includes creating a test schedule having a set of test cases, wherein each test case defines a gas leak location and a gas leak rate. The method includes generating gas sensor arrangement having a number of gas sensors and locations for each of the gas sensors within the worksite. The method includes providing, as inputs to a plume model, at least the locations of each of the gas sensors, the gas leak location and the gas leak rate of each test case of the testing schedule, and the wind speed and the wind direction of each time period of the wind schedule, and receiving, as output from the plume model, predicted gas concentration measurements of each of the gas sensors during each time period of the wind schedule for each test case of the test schedule. The method includes constructing a measurement profile of each of the gas sensors over the forecast time period of interest based on the predicted gas concentration measurements of each of the gas sensors, and using the plume model to determine a predicted gas leak location and a predicted gas leak rate for each test case of the test schedule based at least in part on the measurement profile of each of the gas sensors, the locations of each of the gas sensors, and the stochastic wind model. The method includes evaluating the gas sensor arrangement based on the predicted gas leak location and the predicted gas leak rate.

Certain embodiments of the present disclosure include a method and system comprising planning the location of greenhouse gas leakage detection sensors. Certain embodiments of the present disclosure include an edge device that is part of a cloud-based computing environment, the edge device comprising a system for greenhouse gas leakage management configured to plan the location of greenhouse gas leakage detection sensors or detect source and/or rate of gas leakage. Certain embodiments of the present disclosure include a method for greenhouse gas leakage management, comprising using real-time data from placed sensors to establish a gas leak source. In embodiments of the disclosure, the detection sensors comprise methane detection sensor and/or Optical Gas Imaging (OGI) cameras.

Various refinements of the features noted above may be undertaken in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings, in which.

DETAILED DESCRIPTION

Figure 1:
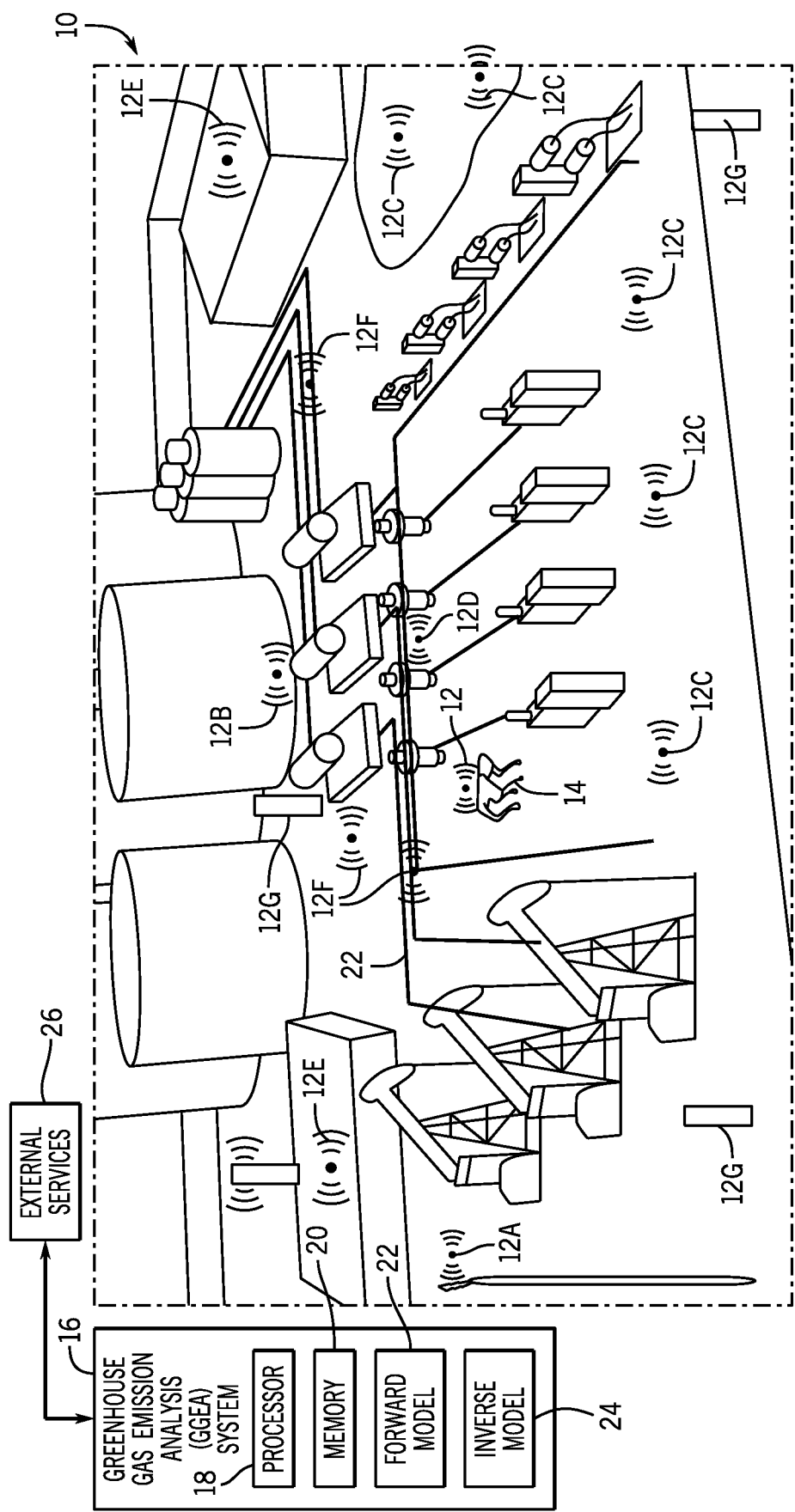
FIG. 1 illustrates an example oil and gas worksite having a plurality of sensors and a greenhouse gas emission analysis (GGEA) system that may be used to monitor greenhouse gas emissions at an oil and gas worksite, in accordance with embodiments of the present disclosure.

One or more specific embodiments of the present disclosure will be described below. These described embodiments are only examples of the presently disclosed techniques. Additionally, in an effort to provide a concise description of these embodiments, some features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

As used herein, the terms "connect," "connection," "connected," "in connection with," and "connecting" are used to mean "in direct connection with" or "in connection with via one or more elements"; and the term "set" is used to mean "one element" or "more than one element." Further, the terms "couple," "coupling," "coupled," "coupled together," and "coupled with" are used to mean "directly coupled together" or "coupled together via one or more elements."

In addition, as used herein, the terms "real time", "real-time", or "substantially real time" may be used interchangeably and are intended to describe operations (e.g., computing operations) that are performed without any human-perceivable interruption between operations. For example, as used herein, data relating to the systems described herein may be collected, transmitted, and/or used in control computations in "substantially real time," such that data readings, data transfers, and/or data processing steps occur once every minute, few minutes, second, once every 0.1 second, once every 0.01 second, or even more frequent, during operations of the systems (e.g., while the systems are operating). In addition, as used herein, the terms "automatic" and "automated" are intended to describe operations that are performed are caused to be performed, for example, by a greenhouse gas emission analysis system (i.e., solely by the greenhouse gas emission analysis system, without human intervention). As used herein, a "gas sensor", a "gas concentration sensor", a "gas emission sensor", a "leaked gas sensor", a "gas leak detection sensor", and related terms, refer to a sensor that measures the concentration of a leaked gas of interest within a domain of interest (e.g., a worksite).

An aspect of the present disclosure is to enable the placement of methane leakage detection sensor for oil and gas production facilities. Because the emitted gas is lost from the production stream, and because methane is a relatively potent greenhouse gas, fugitive emissions of natural gas are economically and environmentally detrimental. Existing methods of gas emission detection are relatively expensive, as they generally involve either a large amount of human resources or an exorbitant amount of expensive equipment to detect gas leaks. Hence, it is desirable to have a systematic solution, based on numerical modeling, to plan the location of gas sensors (e.g., methane leak detection sensors, other types of gas leak detection sensors) in an optimal way, such that the plan covers as many potential leak sources in a facility as possible, while maintaining economic considerations (e.g., sensor cost, human resource costs). Another aspect of the present disclosure is to enable the prediction of a location and a leak rate of a gas leak within an oil and gas production facility based on measurements collected by gas leak sensors disposed within the facility and prevailing wind information.

With the foregoing in mind, present embodiments are directed to a greenhouse gas emission analysis (GGEA) system that includes at least one model (e.g., a plume simulation model), which may be described herein as mathematical, numerical, and/or computer-implemented models for simulating gas leaks under various wind conditions. The GGEA system can be applied in a number of different manners to enable gas leak management on a worksite, such as an oil and gas exploration worksite, an oil and gas processing facility, a chemical processing or manufacturing facility, or any other worksite in which the detection and management of greenhouse gas emissions is desirable. The GGEA system is generally designed to receive a number of inputs, and then to run a simulation or workflow based on the at least one model, to determine one or more outputs related to gas leak detection based on the simulation. For example, in an embodiment, the GGEA system is provided with a number of inputs related to the location and leak rate of a gas leak to be simulated on the worksite, information regarding the wind at the worksite, and locations of gas sensors disposed about the worksite, and the GGEA system uses these inputs, in combination with the at least one model, to output simulated or expected gas concentrations that would be detected by each of the gas sensors at each of their respective locations as a result of the simulated gas leak. In another embodiment, the GGEA system is provided with a number of inputs related to locations of gas sensors disposed about the worksite, gas sensing measurements collected by each of these gas sensors, and information regarding the wind at the worksite, and the greenhouse gas emission analysis system uses these inputs, in combination with the at least one model, to output a predicted location and leak rate of a gas leak on the worksite. Additionally, in certain embodiments, GGEA system may utilize the at least one model to determine optimal gas sensor placement for effective greenhouse gas emission detection on the worksite.

FIG. 1 illustrates an example oil and gas worksite 10 that includes a plurality of sensors 12 that may be used to monitor greenhouse gas emissions at the oil and gas worksite 10. For example, as illustrated in FIG. 1, in certain embodiments, the sensors 12 may include flare monitors 12A, tank sensors 12B, gas concentration monitors 12C, compressor health monitors 12D, structural monitors 12E, process monitors 12F, and/or meteorological sensors 12G. However, in other embodiments, the sensors 12 may include other types of sensors capable of providing data relating to greenhouse gas emissions. Furthermore, other types of data may be used to monitor greenhouse gas emissions at the oil and gas worksite 10, such as the time of day when the detection occurred and the sunrise/sunset time on that day, among other information.

Although described primarily herein as pertaining to oil and gas worksites 10, the term "oil and gas worksite" is intended to include any worksite 10 in which oil and/or gas is processed in any manner, and from which fugitive gas emissions may occur. Indeed, the embodiments described herein include systems and methods for identifying placement of fugitive gas emissions sensors from any types of worksites 10 including, but not limited to, emissions of natural gas from well pad equipment or any point in delivery of gas to a point of use. In addition, the embodiments described herein may be applied to other types of gases (e.g., other greenhouse gases, carbon dioxide, nitrous oxide, sulfur dioxide, fluorinated gases) or fluids (e.g., smoke, volatile organic compounds, oil and gas products) emitted from other types of worksites 10. In general, the embodiments described herein include placing one or more sensors 12 described above around an oil and gas worksite 10 as illustrated in FIG. 1. Collectively, the sensors 12 provide continuous measurement of fugitive and vented greenhouse gas emissions, as well as other conditions (e.g., weather conditions, process conditions, structural conditions), with respect to the worksite 10. In addition, as illustrated in FIG. 1, in certain embodiments, one or more of the sensors 12 described herein may be mounted to a mobile platform or truck 14, for example, an unmanned aerial vehicle (e.g., a drone), a mobile robot (e.g., a Spot robot), or any other relatively agile mobile platform configured to move about an oil and gas worksite 10, carrying one or more sensors 12 that can detect relevant data relating to greenhouse gas emissions that may be occurring at the oil and gas worksite 10, as described in greater detail herein.

For the embodiment illustrated in FIG. 1, the various sensors 12 disposed in and around the worksite 10 are communicatively coupled to a greenhouse gas emission analysis (GGEA) system 16 and configured to provide sensor data to the GGEA system during operation. For example, certain of the sensors 12 may be communicatively coupled to the GGEA system 16 via a suitable wired connection (e.g., Ethernet), while other of the sensors 12 may be communicatively coupled to the GGEA system 16 via a suitable wireless connection (e.g., Wi-Fi, Bluetooth). The GGEA system 16 includes at least one processor 18 (e.g., a central processing unit (CPU)) and at least one memory 20 (e.g., random access memory (RAM), read-only memory (ROM), solid-state disk (SSD), flash memory). In addition to storing computer processor-executable instructions of the GGEA system 16, the memory 20 stores one or more models. In some embodiments, the one or more models may include a forward model 22 and/or an inverse model 24, as discussed in greater detail below.

In some embodiments, the hardware of the GGEA system 16 may include a microprocessor, a microcontroller, a processor module or subsystem, a programmable integrated circuit, a programmable gate array, a digital signal processor (DSP), or another control or computing device. Alternatively or additionally, the at least one processor 18 may include discrete electronic components coupled to a printed circuit board, integrated circuitry (e.g., Application Specific Integrated Circuits (ASICs)), and/or programmable logic devices (e.g., a Field Programmable Gate Arrays (FPGAs)).

In certain embodiments, the GGEA system 16 may be communicatively coupled to one or more external services 26 to receive other data (e.g., meteorological data, solar intensity data, time of day data, worksite operation schedules) used by the GGEA system 16 during operation. In certain embodiments, the GGEA system 16 may be partially or entirely disposed within a cloud-based computing system. As noted above, in various embodiments, the GGEA system 16 utilizes the models 22 and/or 24, in combination with particular inputs, to simulate or model gas leaks within the worksite 10.

In certain embodiments, the one or more models 22 and 24 may be implemented as computer program logic for use with the at least one processor 18. The computer program logic may be embodied in various forms, including a source code form or a computer executable form. Source code may include a series of computer program instructions in a variety of programming languages (e.g., an object code, an assembly language, or a high-level language such as C, C++, or JAVA). The computer instructions may be distributed in any form as a removable storage medium with accompanying printed or electronic documentation (e.g., shrink wrapped software), preloaded on the GGEA system 16 (e.g., on system ROM or fixed disk), or distributed from a server or electronic bulletin board over a communication system (e.g., the Internet or World Wide Web). In addition, in certain embodiments, the disclosed techniques may be implemented via an edge device that is part of a cloud-based computing environment, and the computer program logic may be executed by the edge device in the cloud-based computing environment.

As noted above, in certain embodiments, the GGEA system 16 is configured to receive information regarding a leak to be simulated, the prevailing wind conditions, and the locations of gas sensors 12 within the worksite 10, and based on a simulation, provide a respective concentration of the leaked gas that would be detected by the gas sensors 12. In some embodiments, the GGEA system 16 applies a workflow using the forward model 22, in accordance with Equation 1:

$$MEAS = f(LOCS, SOURCE, WIND) \quad \text{Equation 1}$$

wherein
LOCS is an array having dimensions [m 3], where m is the number of gas sensors 12 (e.g., sample locations) to be simulated within the worksite, and where each sensor 12 of the LOCS array includes respective x, y, and z values defining the simulated location of the gas sensor within a 3D volume (e.g., a sub-domain) of the worksite 10;

SOURCE is an array or set of values describing the location ($S_x$, $S_y$, and $S_z$) of the simulated gas leak, as well as a constant leak rate ($S_r$) of the simulated gas leak, within the worksite 10;

WIND is an array or set of values describing a prevailing wind model at the worksite 10, which may include, but is not limited to: wind speed ($W_s$), wind direction ($W_d$), wind variability over time ($W_t$);

MEAS is an array having dimensions [m 1], where each value indicates a respective, predicted or estimated leaked gas concentration (e.g., in parts-per-million (ppm) or kilograms per cubic meter ($kg/m^3$)) that would be measured by each of the m gas sensors 12; and f is a function that defines the forward model, which relates the inputs (e.g., LOCS, SOURCE, and WIND) to the output (e.g. MEAS).

Additionally, in some embodiments, the forward model 22 (f), may accept other additional inputs, including but not limited to: an initial plume jet momentum and direction; a composition and/or density of the leaking gas; a detailed 2D or 3D worksite plan, or an aerial or satellite view of the worksite, indicative of placement of structures, obstructions such as tanks, buildings, trees, hills or valleys, walls, and so forth. Additional atmospheric information, such as vertical wind profile, solar radiation intensity, vertical temperature profile, humidity, cloud cover, presence of inversion layers, atmospheric stability class, as well as other suitable atmospheric or meteorological data, may also be provided as inputs to the forward model 22 in certain embodiments.

Figure 2:
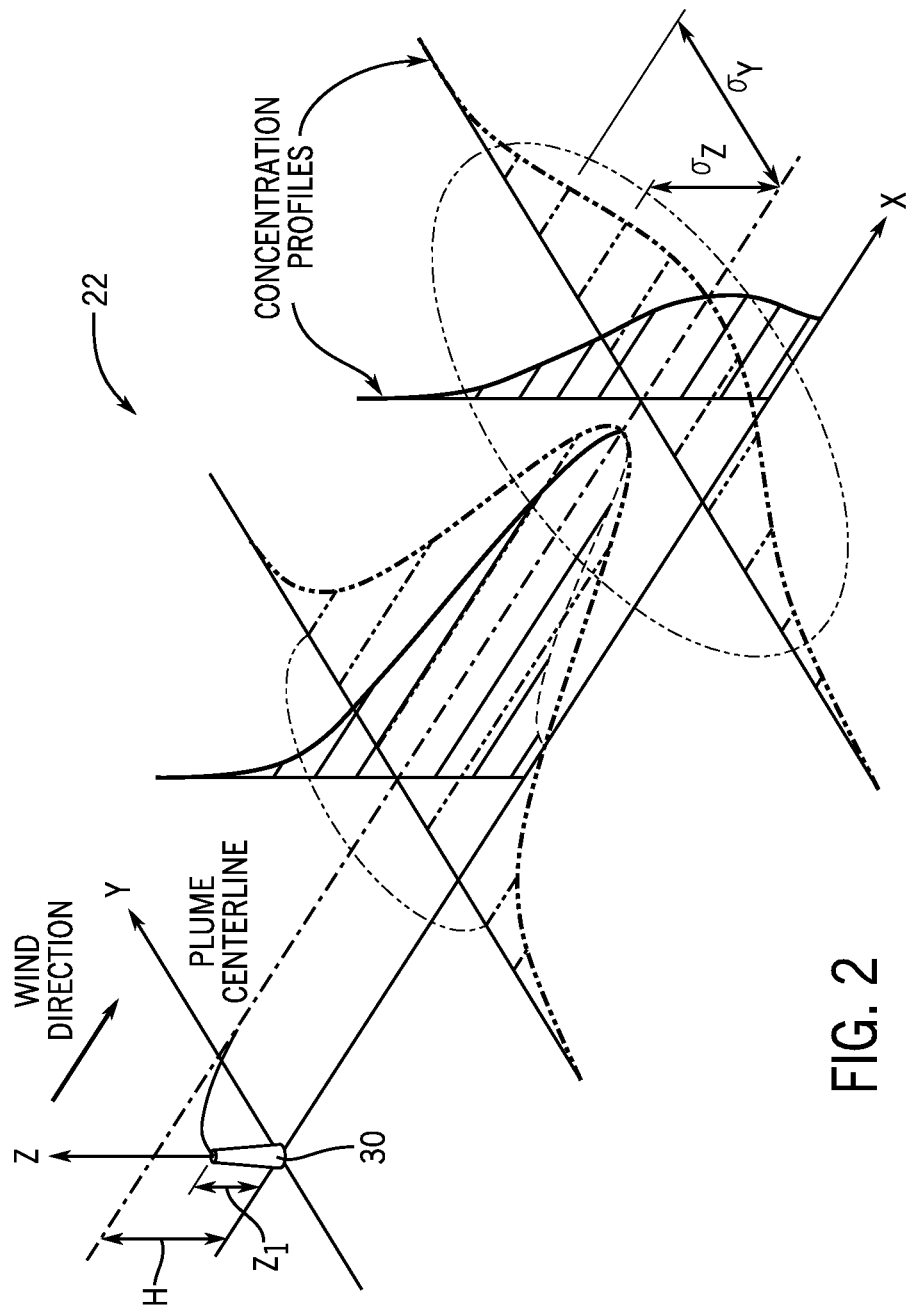
FIG. 2 illustrates an example forward model of the GGEA system as a Gaussian plume model, in accordance with embodiments of the present disclosure.

FIG. 2 illustrates an example embodiment of the forward model (f) 22, which is a Gaussian plume dispersion model that is configured using parameters of a particular greenhouse gas (e.g., methane). The embodiment of the forward model 22 illustrated in FIG. 2 provides a steady solution that, for a continuous fixed rate leak source and known wind properties (e.g., fixed wind direction ($W_d$) and fixed wind speed ($W_s$)), yields the gas concentration expected to be measured at an arbitrary point in space within the worksite 10. For the illustrated forward model 22, a simulated gas leak source 30 is disposed at height $Z_1$ and combined with the aforementioned wind information to yield a 3D simulated gas plume having a plume centerline H. This simulated gas plume yields simulated 3D concentration profiles, which can be used to estimate or predict measurement of a simulated gas sensor disposed at a given location (e.g., defined with respect to the plume centerline) under the leak and wind conditions of the model. In other embodiments, the forward model 22 may instead include or rely on other, more involved methods (e.g., to address non-continuous steady-rate leaks), and these methods may be based on numerical simulation, computational fluid dynamics (CFD), or other suitable computational or modeling methods. For example, in some embodiments, the forward model 22 may be a plume model based on computational fluid dynamics (CFD), a plume model based on trained machine learning models, or a plume model for flow around structures. It may be appreciated that such methods may capture initial plume generation and better handle the effect of obstacles in the plume path, in certain embodiments.

Figure 3:
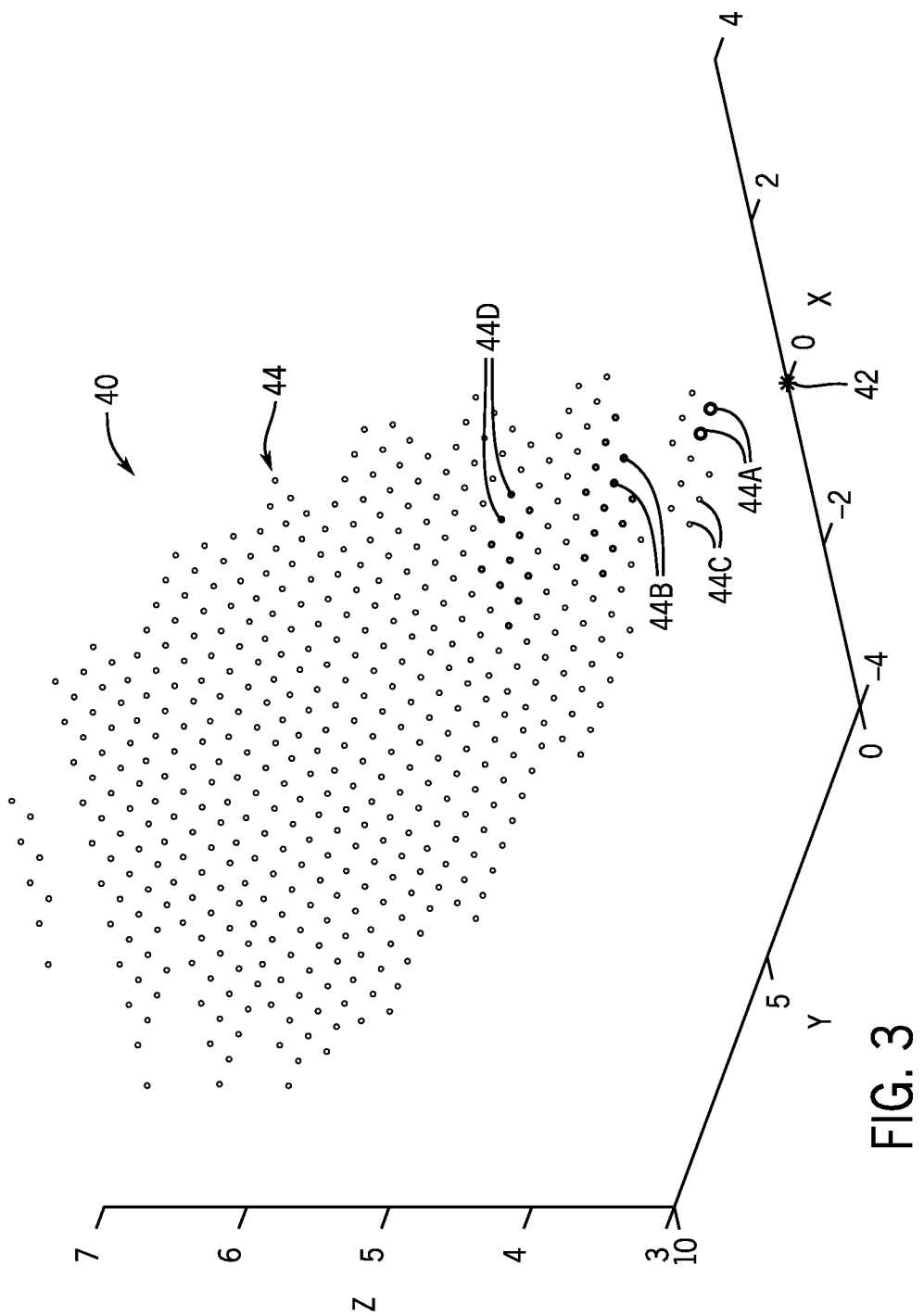
FIG. 3 illustrates the forward model response for an example gas leak, in accordance with embodiments of the present disclosure.

FIG. 3 is a 3D graph 40 visually depicting the output of the embodiment of the forward model 22 for an example simulated gas leak. The volume represented by the graph 40 corresponds to the 3D volume of the worksite 10, while the point 42 represents the source location of the gas leak within the 3D volume of the worksite 10. Additionally, for the example depicted by FIG. 3, the wind direction ($W_d$) is fixed at 90 degrees, the wind speed is fixed at 5 kilometers per hour, and the constant leak rate is set to 1 kilogram per hour. Each of the points 44 within the graph 40 represent the response of the example forward model 22 of FIG. 2 at the indicated location. That is, each of the points 44 represent an entry within the MEAS array output by the forward model 22 in response to the aforementioned inputs. As such, each of the points 44 of the 3D graph represents an expected leaked gas concentration that would be measured by a sensor 12 disposed at the illustrated location within the 3D volume of the worksite 10. Additionally, each of the points 44 are illustrated using different point styles, in which 44A represents relatively highest gas concentrations, 44B and 44D represents relatively lower gas concentrations, and 44C represents even lower gas concentrations within the 3D volume of the worksite 10, as predicted by the forward model 22.

In certain embodiments, the GGEA system 16 is additionally or alternatively configured to receive information regarding the locations of the sensors 12 within the worksite 10, the concentrations of leaked gas measured by each of these sensors 12, and the wind conditions at the worksite 10, and based on a simulation that utilizes the inverse model 24, provide a source location and leak rate of a gas leak within the worksite 10. Like the forward model (f) 22, the inverse model (g) 24 may be derived from a Gaussian plume dispersion model using parameters for a particular greenhouse gas (e.g., methane), or another suitable model or method, as discussed above. In some embodiments, the inputs and outputs may represent hypothetical or simulated data, while in other embodiments, the inputs correspond to actual measurements of the gas sensors 12 disposed at specific locations within the worksite 10, and the outputs correspond to a predicted gas leak within the worksite 10.

In some embodiments, to identify the location and leak rate of a simulated or actual gas leak within the worksite 10, the GGEA system 16 may apply a second workflow using the inverse model 24, in accordance with Equation 2:

$$\text{SOURCE} = g(\text{MEAS}, \text{LOCS}, \text{WIND}) \quad \text{Equation 2}$$

wherein
SOURCE is an array or set of values describing the location ($S_x$, $S_y$, and $S_z$) of the gas leak within a 3D volume (e.g., a sub-domain) of the worksite 10, as well as a constant leak rate ($S_r$) of the simulated gas leak;
LOCS is an array having dimensions [m 3], where m is the number of gas sensors 12 (e.g., sample locations) positioned within the worksite, and where each sensor 12 of the LOCS array includes respective x, y, and z values defining the location of the gas sensor within the worksite 10;
MEAS is an array having dimensions [m 1], where each value indicates a respective leaked gas concentration (e.g., in parts-per-million (ppm) or kilograms per cubic meter ($kg/m^3$)) measured by each of the m gas sensors 12;
WIND is an array or set of values describing a prevailing wind model at the worksite 10, which may include, but is not limited to: wind speed ($W_s$), wind direction ($W_d$), wind variability of time ($W_t$); and
g is a function that defines the inverse model 24, which relates the inputs (e.g., MEAS, LOCS, and WIND) to the output (e.g. SOURCE).

Additionally, in some embodiments, the inverse model 24 (g) may accept other additional inputs, including but not limited to: an initial plume jet momentum and direction; a composition and/or density of the leaking gas; detailed 2D or 3D plan of the worksite, or an aerial or satellite view of the worksite, indicative of placement of structures, obstructions such as tanks, buildings, trees, hills or valleys, walls, and so forth. Additional atmospheric information, such as vertical wind profile, solar radiation intensity, vertical temperature profile, humidity, cloud cover, presence of inversion layers, atmospheric stability class, as well as other suitable atmospheric or meteorological data, may also be provided as inputs to the inverse model in certain embodiments. As noted, in certain embodiments, the inverse model 24 can be used to model the source location and leak rate of an actual gas leak on the worksite 10 when the locations and the measurements of the actual sensors 12 are known. However, as discussed below, in some embodiments, the GGEA system 16 may also be configured to determine the optimal number of sensors 12, as well as their optimal locations within the worksite 10, based on inputs related to the worksite 10, the forward model 22, and/or the inverse model 24.

Leak Source Identification

As noted, in certain embodiments, the GGEA system 16 is configured to identify or predict a location and a leak rate of a gas leak based on gas concentration measurements collected by the gas sensors 12 disposed at particular locations within the worksite 10. In embodiments of the disclosure, the leak source identification problem can be considered a multi-variate optimization problem (e.g., for source location, source leak rate, and other elements of interest) given a number of gas sensors 12 at known locations within the worksite 10 with known gas concentration measurements collected over some time period of interest ($d_t$). Further, the wind model (WIND), which describes the wind behavior over the time period of interest, is also assumed known for this use case. Additionally, as noted herein, in certain embodiments, the GGEA system 16 may also receive other inputs that can be used to define or constrain the forward and/or inverse models.

Figure 4:
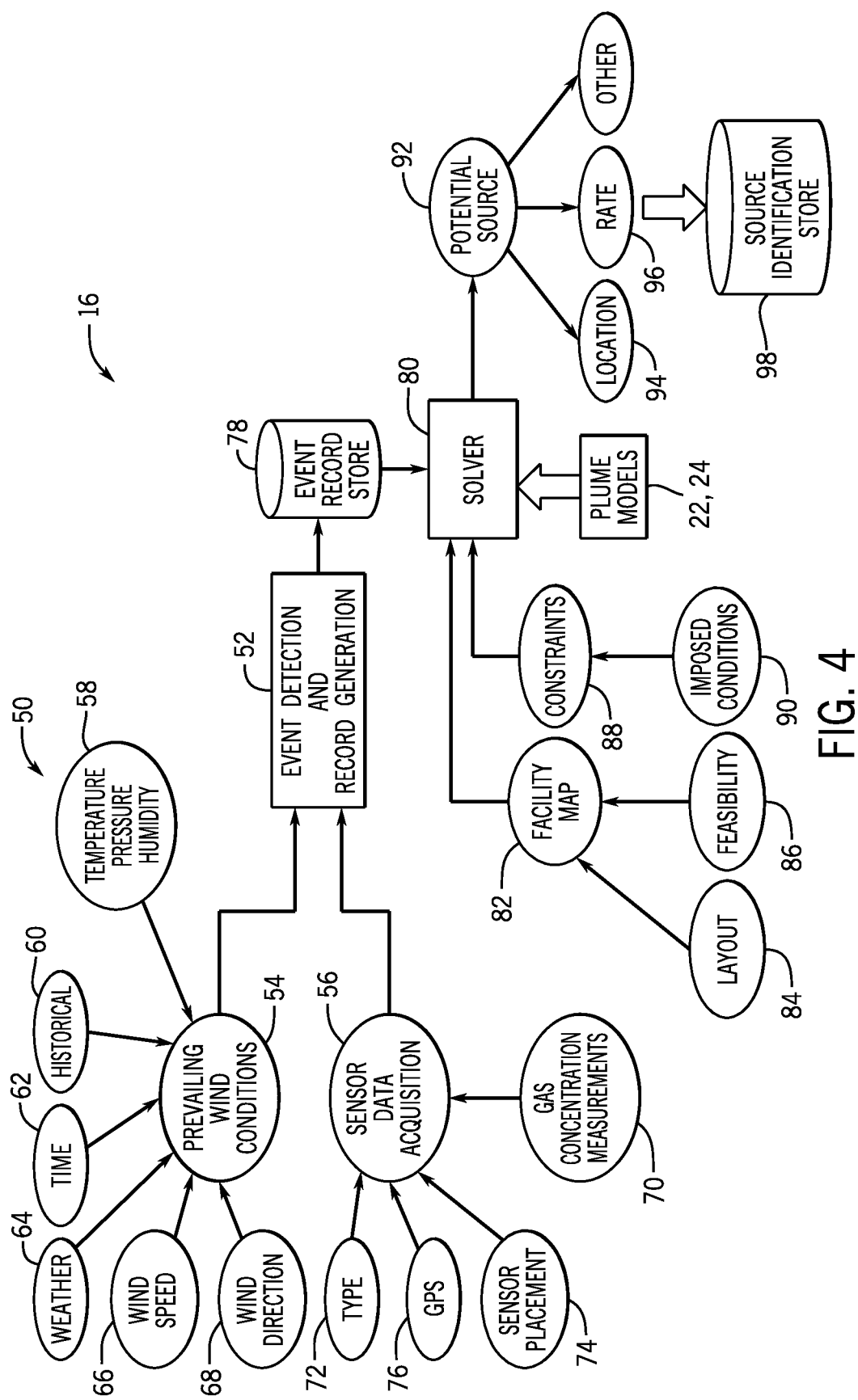
FIG. 4 illustrates an example data schema of the GGAE system for source location identification of a gas leak, in accordance with embodiments of the present disclosure.

FIG. 4 is a data schematic 50 for an embodiment of the GGEA system 16. For the embodiment illustrated in FIG. 4, the GGEA system 16 includes an event detection and record generation component 52 that is designed to receive prevailing wind condition information 54 and gas sensor data 56, and to convolute these into valid event records for further analysis, as discussed below. As illustrated, the event detection and record generation component 52 may receive prevailing wind condition information 54 from one or more of the wind sensors 12 disposed at the worksite, from a suitable external weather service, or another suitable source. As indicated, example prevailing wind condition information 54 may include information related to temperature/pressure/humidity 58, historical wind/weather data 60, time data 62, current or forecasted weather conditions 64, measured wind speed 66, and/or measured wind direction 68. Example gas sensor data 56 may include gas concentrations measurements 70, information related to the type 72 of each gas sensor, and information related to the location of each gas sensor (e.g., sensor placement 74, global positioning system (GPS) coordinates 76 of each gas sensor). As discussed below, the event detection and record generation component 52 is designed to generate and store valid event records in an event record store 78 (e.g., a database) of the GGEA system 16.

For the embodiment illustrated in FIG. 4, the GGEA system 16 includes a solver 80 that is designed to receive information from a number of different sources, and to provide at least some of this information as inputs to at least one model or workflow disclosed herein to determine useful information related to managing gas leaks. For the illustrated embodiment, the solver 80 receives or retrieves valid event records from the event record store 78. The solver 80 also receives facility map information 82, which may include information related to the layout 84 of the worksite or information related to leak feasibility 86 (and lack of feasibility) for different portions (e.g., sub-domains) of the worksite. The illustrated solver 80 also receives constraint information 88, which may include imposed conditions 90 that should be respected during the analysis. For the illustrated embodiment, the solver 80 utilizes plume models (e.g., the forward model 22 and/or the inverse model 24) to determine or predict potential gas leak source information 92, such as the predicted location 94 of the gas leak, the predicted leak rate 96 of the gas leak, or other useful information. Additionally, the GGEA system 16 includes a source identification store 98 (e.g., a database), which is designed to store the potential gas leak source information 92 for later use and evaluation. In some embodiments, the event detection and record generation component 52 and the solver 80 may be implemented as computer instructions (e.g., software) stored in the at least one memory 20 and executed by the at least one processor 18 of the GGEA system 16 illustrated in FIG. 1.

Figure 5:
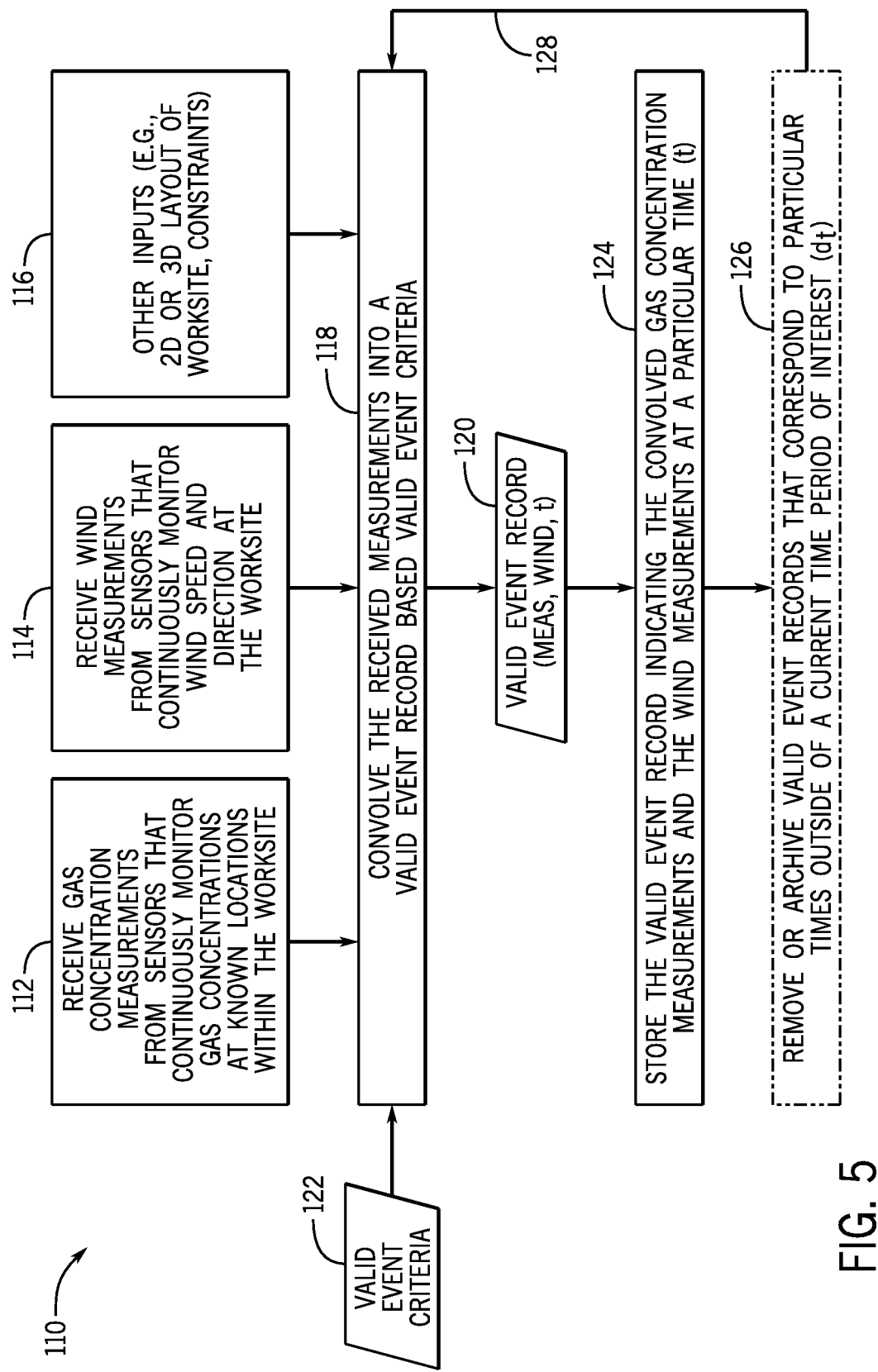
FIG. 5 is a flow diagram illustrating a process whereby the GGEA system receives and processes sensor information into valid event records, in accordance with embodiments of the present disclosure.

FIG. 5 is a flow diagram illustrating an embodiment of a process 110 whereby the event detection and record generation component 52 receives and processes information into valid event records for further processing by the solver 80. The process 110 may be implemented as computer-executable instructions that are stored in the at least one memory 20 and executed by the at least one processor 18 of the GGEA system 16. The process 110 includes receiving (block 112) gas concentration measurements from gas sensors 12 that continuously monitor gas concentrations at known locations within the worksite. The process 110 includes receiving (block 114) wind measurements from wind sensors 12 that continuously monitor wind speed and direction at the worksite. In some embodiments, the process 110 may also include receiving (block 116) other inputs, such as a 2D or 3D layout of the worksite or constraints, which are discussed in greater detail below.

For the embodiment illustrated in FIG. 5, the process 110 includes the event detection and record generation component 52 convolving (block 118) a portion of the received gas concentration and wind measurements into a valid event record 120 based on valid event criteria 122. Convolution may involve one or more steps. For example, in certain embodiments, convolution involves at least synchronizing the gas concentration measurements and the wind measurements based on the time at which the measurements were collected. In some embodiments, convolution may involve data smoothing over a small period of interest. In some embodiments, convolution may involve removing or ignoring certain gas concentration measurements, such as gas concentration measurements below a predefined threshold value and/or measurements collected during unfavorable wind conditions, as defined by the valid event criteria. In some embodiments, the valid event criteria may be defined by a user or designer of the GGEA system 16. It may be appreciated that, while wind measurements are discussed in particular, the convolution of block 118 may additionally involve the convolution of other weather sensor data (e.g., solar radiation sensors, rain sensors) and/or meteorological data (e.g., solar intensity data, rain data) received from external weather services.

For the embodiment illustrated in FIG. 5, the valid event record 120 includes convolved gas concentration measurements (MEAS) and wind information (WIND) collected (e.g., by the gas and wind sensors 12) at a particular time (t). The process 110 continues with the event detection and record generation component 52 storing (block 124) the valid event record 120 in the event record store 78, as discussed above. In certain embodiments, the event detection and record generation component 52 may intermittently remove or archive (block 126) valid event records 120 from the event record store 78 that correspond to times outside of a current time period of interest (e.g., a predefined rolling time window). As indicated by the arrow 128, the event detection and record generation component 52 may continue to convolute incoming gas concentration and wind measurements to generate and store new valid event records. It may be appreciated that each discernible detection (e.g., each valid event record) provides information as to a possible source. This means that valuable information can be gleaned from a valid event record having a gas concentration measurement indicating that the gas sensor made no detection despite favorable wind conditions. For example, in certain situations, a gas sensor with zero reading under favorable wind conditions also provides useful information for leak source identification, and may be included as part of a valid event record.

Figure 6:
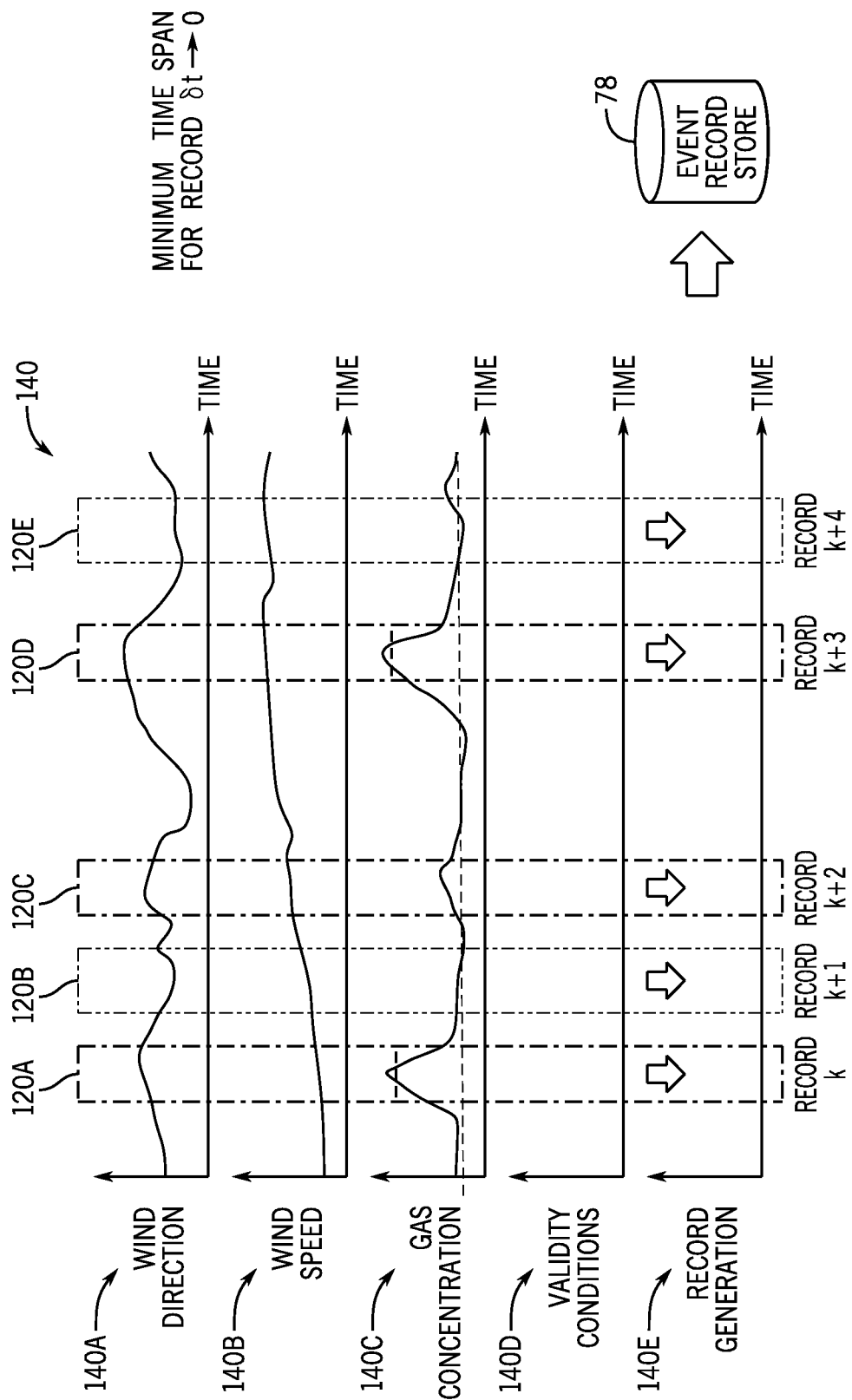
FIG. 6 illustrates sensor and wind data convolution to generate valid event records, in accordance with embodiments of the present disclosure.

FIG. 6 is a set of graphs 140 illustrating example convolutions, in which an embodiment of the event detection and record generation component 52 receives and processes gas concentration measurements and wind measurements to generate valid event records. The graphs 140 include: graph 140A that illustrates measured wind direction at the worksite over time, graph 140B that illustrates measured wind speed at the worksite over time, graph 140C that illustrates measured gas concentration at a location in the worksite, graph 140D illustrates validity conditions that are part of the valid event criteria 122 discussed above, and graph 140E illustrates the collection of valid event records 120A-E from the incoming gas concentration and wind data. Gas concentration and wind data convolution is used to identify valid event records, which indicate both the gas concentration measurement and the prevailing wind conditions at a specific time. It may be appreciated that, while a single gas concentration sensor measurement is illustrated in FIG. 6, this convolution process may be applied to the gas concentration measurements of all gas sensors disposed at the worksite.

As noted above, in some embodiments, the convolution procedure includes temporal synchronization, and may include smoothing of the gas concentration measurements, the wind measurements, or both. For the embodiment illustrated in FIG. 6, based on the validity conditions of the valid event criteria 122, the event detection and record generation component 52 convolutes portions of the wind information from graphs 140A and 140B with portions of the gas concentration measurement of 140C to generate valid event records 120A, 120B, 120C, 120D, and 120E. In some embodiments, the validity conditions may be defined by the user or designer of the GGEA system 16, and these conditions may be related to steady wind conditions, low variability in readings, minimum time span for each event record, or other suitable conditions. For the embodiment illustrated in FIG. 6, it may be appreciated that valid event records 120B and 120C include zero or negligible gas concentration readings; however, as noted above, these valid event records include meaningful data useful in identifying the source of a potential gas leak.

In certain embodiments, the GGAE system 16 may determine or predict the source location and leak rate of a potential gas leak (over period $d_t$) by solving an optimization problem in accordance with Equation 3:

$$\mathrm{argmin} R(X) = \sum_{j=1}^{r} (M_j^{mod}(LOC_j, X, WIND_j) - M_j^{obs})^2$$

$$\mathrm{s.t.} \ x_i^L \le x_i \le x_i^U$$

wherein R(X) is an example cost function, which in this example, is the sum of the squares of the residuals of the mis-match (over r valid event records) between the actual measurement $M_j^{obs}$ at known sensor locations (LOCS) and those established from the forward model $M_j^{mod}$ for the source location and rate given by the control variable set X. In some embodiments, other cost functions may be used, in accordance with the present disclosure. In some embodiments, other parameters in the forward model may be included in this equation as part of the cost function (but are not shown here).

The solutions to the optimization problem represented by Equation 3 provide the potential locations of a gas leak source, as well as the potential leak rate, over period $d_t$ given r valid event records of interest. These solutions may be stored, for example, in the source identification store 98 discussed above, and the time period is subsequently incremented by $t_d$. In some embodiments, the source identification store 98 may be filtered to remove old records, or a weight term may be applied to older records accordingly. A cost function might then reflect a weighted sum of residuals metric. In certain embodiments, the computational time utilized to predict the location and leak rate of a gas leak is less than the delay period by $t_d$. In some embodiments, the cost function may include sum of absolute differences versus other robust norms.

In certain embodiments, the optimization problem may be repeatedly solved over incremental steps (with period $d_t$), as additional valid event records are stored based on recent measurement data received from the gas and wind sensors of the worksite, as discussed above. In embodiments, a source location density map might be constructed (and updated at each step) to visually indicate the most likely location of a gas leak source within the worksite.

In embodiments of the disclosure, little or no information from the gas sensors may indicate non-detection of leaked gas due to prevailing wind conditions, but may not be sufficient to conclude no gas leak exists. Indeed, earlier valid event records may indicate whether a potential leak has been previously identified. Otherwise, one valid event record with notable gas detection may be sufficient to anticipate a gas leak could be present. When the event record store 78 is empty, the detection process can commence from anew, in accordance with the present disclosure.

In some embodiments, the assertion of the source location variables (Sx, Sy, Sz) as integers may limit the possible leak locations to a pre-defined grid, while in some embodiments, feasible leak locations may be mapped by index in the optimization problem directly. Similarly, infeasible regions may be defined by the addition of constraints, such as those discussed below. In either case, the optimization problem can be suitably modified to manage the stipulated conditions. In some embodiments, the GGEA system 16 may include a solver 80 that can readily handle mixed-integer variables, for example, those discussed in *Advances in Metaheuristics for Hard Optimization*, Patrick Siaray and Zbigniew Michalewicz, Eds., Springer, 2007 or *Handbook of Metaheuristics*, Michel Gendreau and Jean-Yves Potvin, Eds., Springer, 2019.

Figure 7:
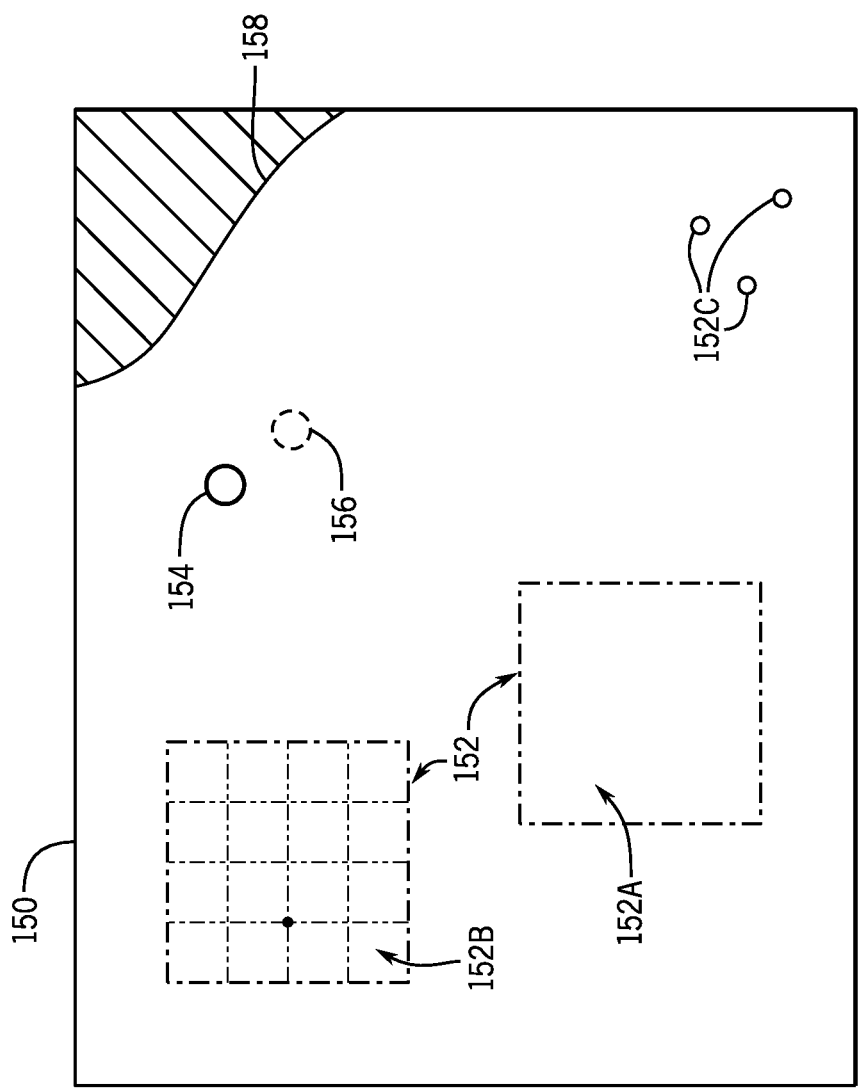
FIG. 7 represents a problem domain representation in two-dimensions (2D), in accordance with embodiments of the present disclosure.
Figure 8:
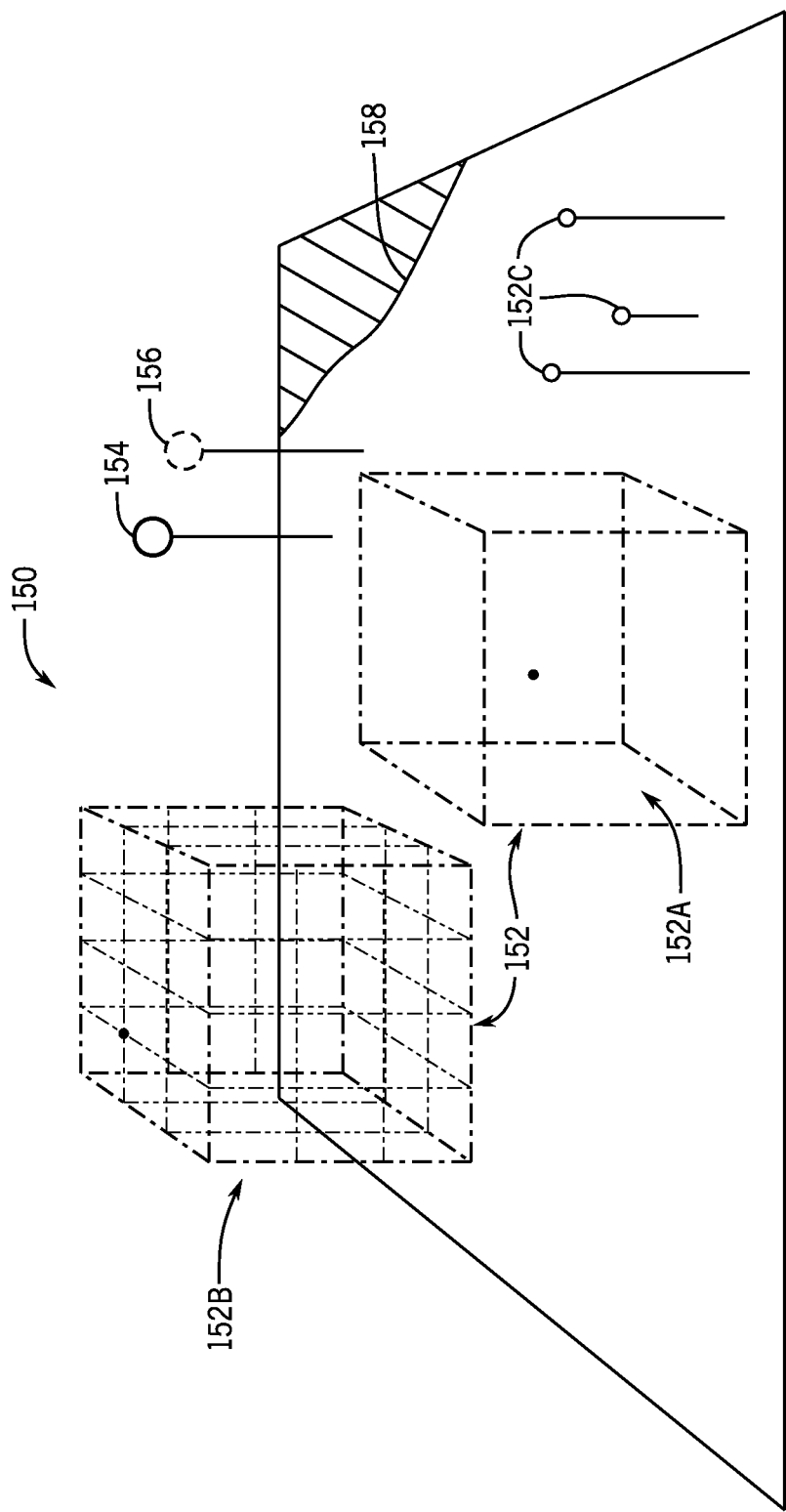
FIG. 8 represents a problem domain representation in three-dimensions (3D), in accordance with embodiments of the present disclosure.

In embodiments of the disclosure, examples of a representative domain of interest 150 (e.g., worksite 10, a facility, a building, a geographic area) with feasible sub-domains 152 are shown in FIGS. 7 and 8. Each of the sub-domains 152 may be defined by a constraint set that indicates feasibility of gas leak locations. Each of the sub-domains 152 may be continuous, discrete, or defined by feasible point locations. The feasible point location implementation permits discrete non-grid-based locations, or a sub-set thereof. The domain of interest 150 may comprise any sub-domain type given the description of the worksite. Thus, the disclosed leak location prediction may include constraints to ensure the leak source location established is feasible. For embodiments without defined constraints, the gas leak source may be identified anywhere within the bounds of the domain of interest 150. Note that the sub-domains 152 may be described in 2D (z-axis invariant) or in 3D, as shown in FIGS. 7 and 8, respectively. In FIG. 7, the location of one gas sensor 154 and one wind meter 156 is shown in plan view, while in FIG. 8, the location of the gas sensor 154 and one wind meter 156 is shown in 3D. In both FIGS. 7 and 8, examples of feasible sub-domains are shown as continuous sub-domains 152A, discrete sub-domains 152B, and point location sub-domains 152C, while the nonlinear constraint boundary 158 may assert or define a non-feasible region (e.g., a river, neighboring land, etc.) that should be excluded from consideration when predicting the location of a gas leak.

The aforementioned convolution of gas and wind sensor data into valid event records is believed to provide better results than attempting to predict gas source locations independently using the sensor data at each time step, as this approach may fail when some gas sensors do not signal detection due to the prevailing direction of the wind. Additionally, including data from multiple valid event records or time steps improves the robustness of the leak source prediction, as more detection events aid the localization process. Moreover, it is recognized that using gas concentration measurements from too few gas sensors may prevent source localization, as there may be insufficient information with which to effectively triangulate the gas leak source.

Record Generation and Source Localization

Figure 9:
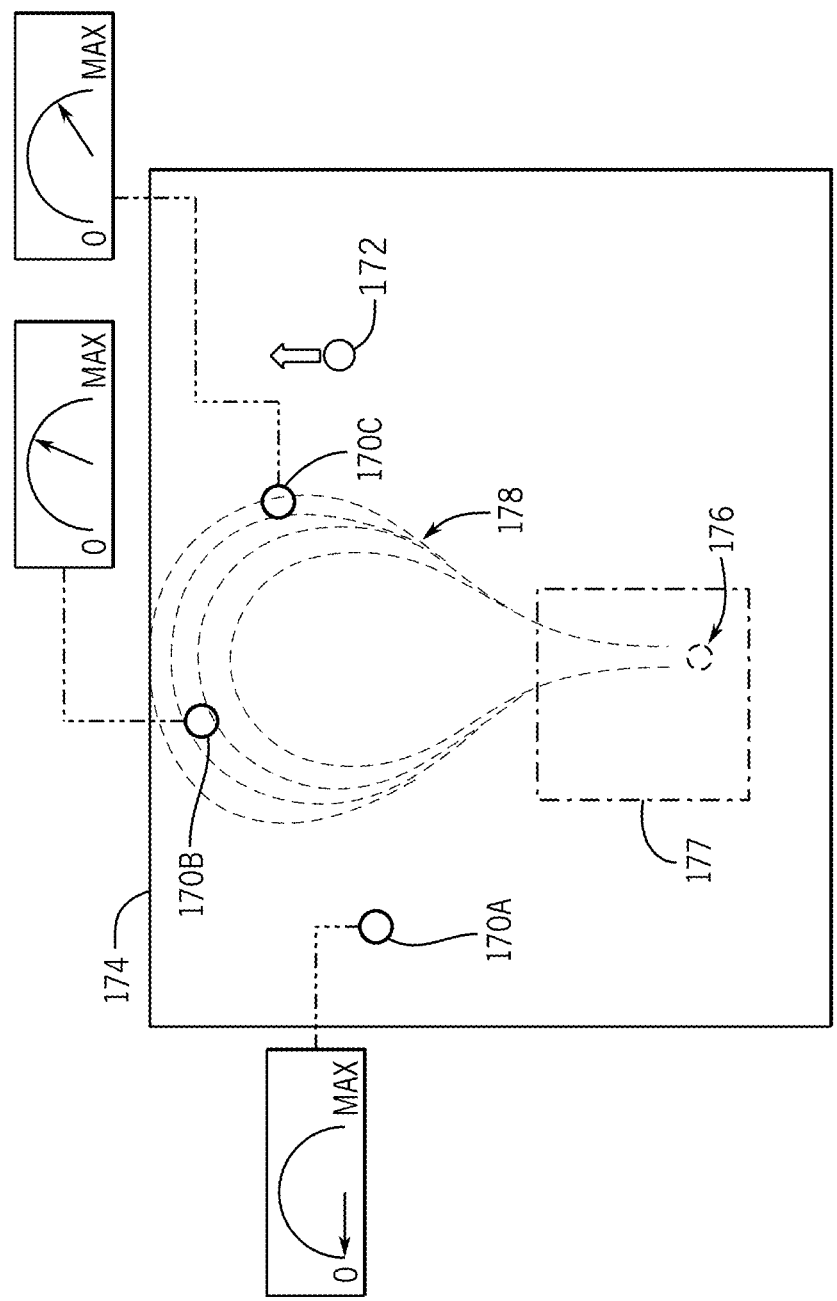
FIGS. 9, 10, and 11 represent examples of fixed gas concentration sensor detection with different wind conditions at different time intervals, in accordance with embodiments of the present disclosure.
Figure 10:
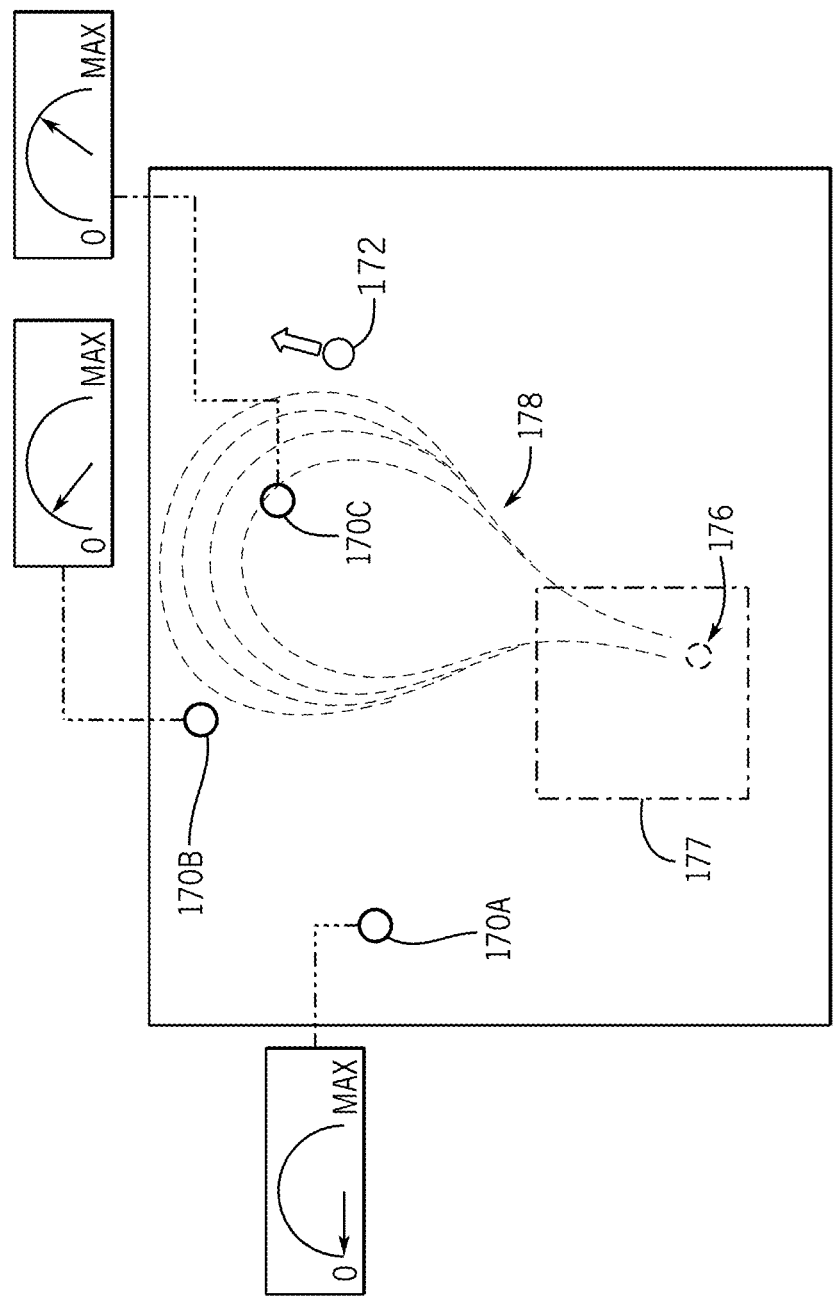
Figure 11:
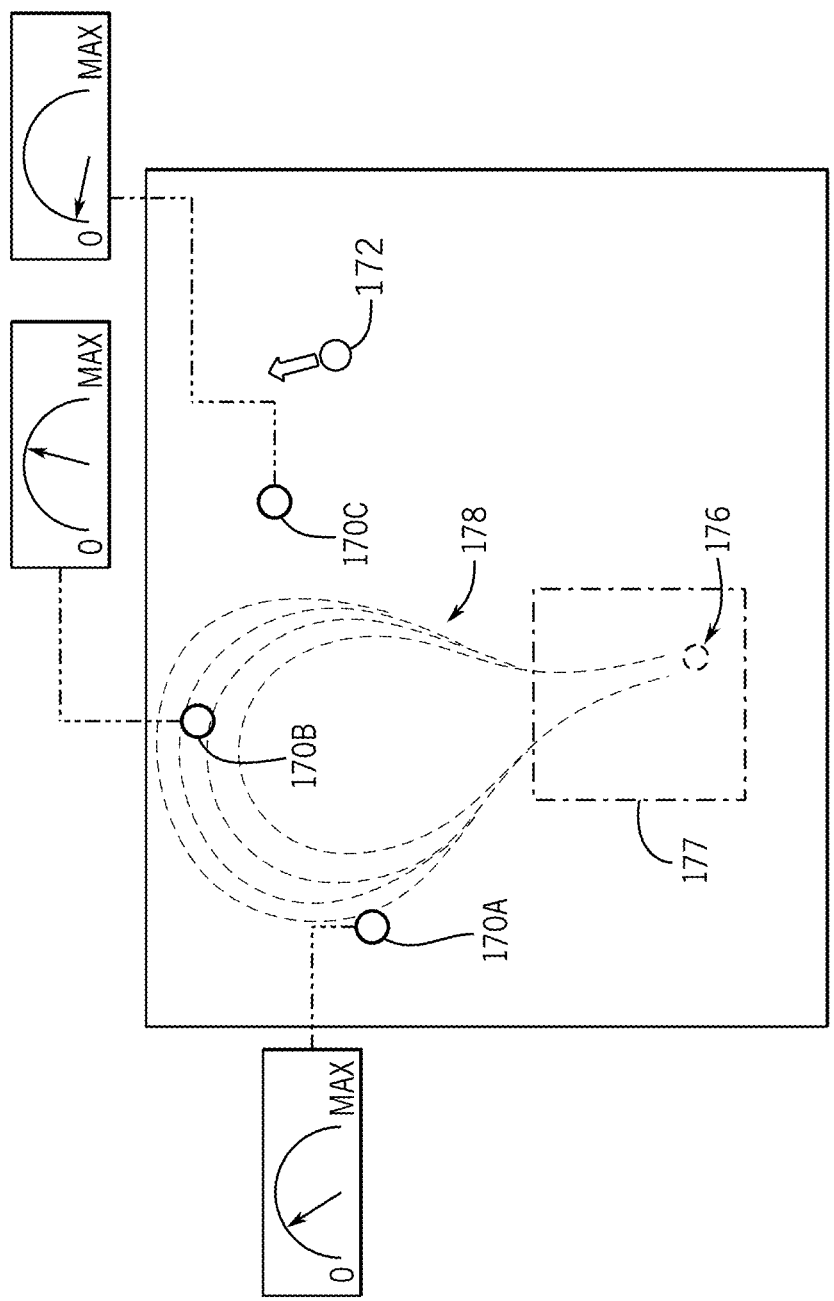

FIGS. 9, 10, and 11 illustrate an example valid event record generation process at changing intervals according to embodiments of the disclosure. Each of these figures illustrates the location of three fixed gas sensors 170 (e.g., gas sensors 170A, 170B, and 170C) and a wind speed and direction meter 172 within a domain of interest 174 (e.g., the worksite) illustrated in plan view. In each of the figures, the known gas leak source 176 is illustrated as being disposed within a feasible continuous sub-domain 177 along with the iso-contours 178 of the leaked gas plume. The figures further indicate gas concentration measurements collected by each gas sensors 170 disposed at the illustrated locations within the domain of interest 174 at a particular time interval. The measurements or readings of the gas sensors positioned outside of the plume range are negligible, as noted by the illustrated gas concentration readings.

In the example of FIG. 9, the gas sensor 170A reading is zero, while the readings of the other two gas sensors 170B and 170C indicate leaked gas detection. As such, for the time interval represented by FIG. 9, each of the gas sensors 170 experience favorable wind conditions, resulting in the creation and storage of three valid event records. In a subsequent time interval represented by FIG. 10, a change in the wind direction results in the gas sensor 170C detecting leaked gas, while gas sensors 170A and 170B demonstrate little or no detection with the given wind direction. In a subsequent time interval represented by FIG. 11, another change in the wind direction results in the gas sensors 170A and 170B detecting leaked gas, while gas sensor 170C demonstrates little or no detection with the given wind direction. As indicated by these figures, meaningful data can be gathered from gas sensors 170, even with low readings. Thus, certain valid event records in this context may include a zero-reading gas concentration measurement, depending on the valid event criteria 122 discussed above.

Optimal Gas Sensor Arrangement

For the embodiments discussed above, the locations of the gas sensors (LOCS) within the worksite 10 are known. However, in certain embodiments, the GGEA system 16 may be used to determine an optimal gas sensor arrangement, which indicates an optimal number of gas sensors to be used to monitor a worksite, as well as optimal locations for each of these gas sensors within the worksite. The optimal gas sensor arrangement generally maximizes leak detection while minimizing the cost involved (e.g., by using the fewest gas sensors, by using the least number of time intervals). For embodiments that enable determination of the optimal gas sensor arrangement, the forward model 22 discussed above may be used. Additionally, information on the topology and layout of the worksite is known, along with the locations of components of the worksite that are feasible or probable to leak, and this information may be provided to the GGEA system 16 to enable determination of gas sensor arrangement, as discussed below.

Figure 12:
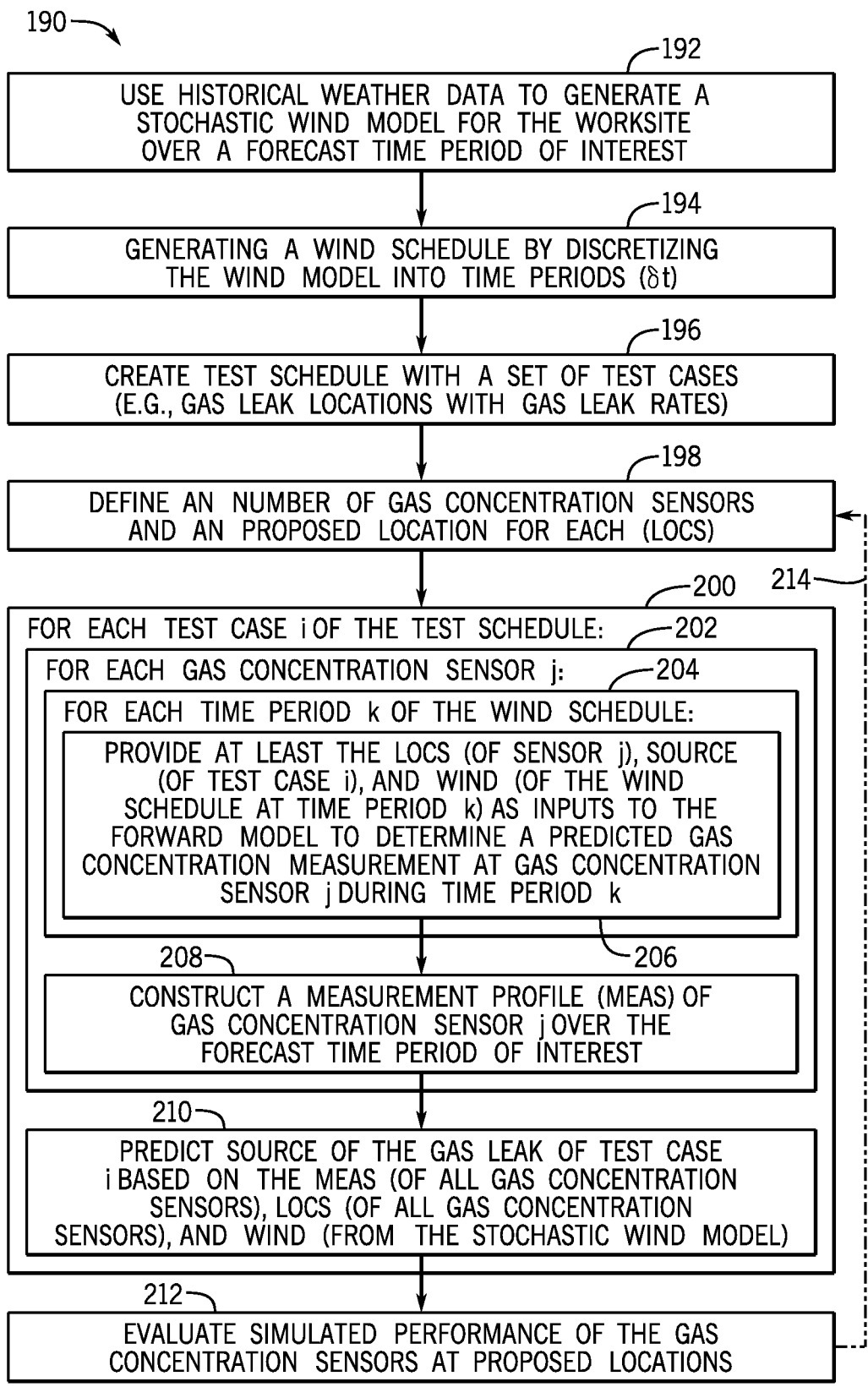
FIG. 12 is a flow diagram illustrating a process by which the GGEA system determines an optimal gas sensor arrangement for a worksite, in accordance with embodiments of the present disclosure.

FIG. 12 is a flow diagram illustrating an embodiment of a process 190 by which the GGEA system 16 determines the optimal gas sensor arrangement for a particular domain of interest (e.g., worksite 10). The process 190 may be implemented as computer-executable instructions that are stored in the at least one memory 20 and executed by the at least one processor 18 of the GGEA system 16, as discussed above. For the illustrated embodiment, the process 190 begins with the GGEA system 16 using (block 192) historical weather data to generate a stochastic wind model for the worksite over a forecast time period of interest, which may be on the order of days. It may be noted that, in some embodiments, a non-stochastic wind model may be generated directly from historical weather data (e.g., using the wind conditions over a set of 12 hour long time periods), and this non-stochastic wind model may be used in lieu of the stochastic wind model for the remainder of the process 190.

For the embodiment illustrated in FIG. 12, the process 190 continues with the GGEA system 16 generating (block 194) a wind schedule by discretizing the wind model into time periods of ∂t. The GGEA system 16 also creates (block 196) a test schedule having a set of test cases, each test case defining a unique combination of a possible leak location and possible leak rate. For example, when there are $n_c$ possible leak locations, each with $n_s$ possible leak rates, there will be $n_d$ test cases in the test schedule, wherein $n_d = n_c \times n_s$. The GGEA system 16 also defines (block 198) an initial number of gas sensors to monitor the worksite, as well as an initial proposed location for each gas sensor. In some embodiments, the initial number and locations of the gas sensors may be defined based on user input, or may be selected at random. In some embodiments, at least three gas sensors may be used to enable leak source triangulation, wherein the gas sensors may be defined at different spatial locations and/or different elevations throughout the worksite.

For the embodiment illustrated in FIG. 12, the process 190 continues with the GGEA system 16 performing a number of actions within a set of nested for—each loops. For the illustrated embodiment, the outer for—each loop 200 iterates through each test case i of the test schedule (as created in block 196), the middle for—each loop 202 iterates through each gas sensor j (as defined in block 198), and the inner for—each loop 204 iterates through each time period k of the wind schedule (as generated in block 194). Accordingly, at block 206, the GGEA system 16 provides at least the location (LOCS) of sensor j, the leak location and leak rate (SOURCE) of test case i, and the wind speed and direction (WIND) of the wind schedule at time period k as inputs to the forward model 22, wherein the forward model 22 responds by outputting a predicted gas concentration measurement at sensor j during time period k based on the leak scenario of test case i. As noted herein, in some embodiments, other inputs may also be provided to the forward model 22, and these inputs may be obtained from historical data, nearby location data, or simulated data (to the extent possible), and then treated in a way analogous to the wind data.

For the embodiment illustrated in FIG. 12, after repeating the actions of block 206 for each of the time periods k of the wind schedule, at block 208, the GGEA system 16 constructs a respective measurement profile (MEAS) for each sensor j over the forecast time period of interest. In embodiments, these measurement profiles serve as a proxy to the real-time gas concentration measurements that would be provided by an actual gas sensor at the defined location under the wind and test case conditions.

For the embodiment illustrated in FIG. 12, after constructing the respective measurement profile (MEAS) for each sensor j over the forecast time period of interest, for each test case i of the test schedule, the GGEA system 16 uses the leak source identification process discussed above to predict (block 210) a leak location and a leak rate (SOURCE) based on the measurement profiles (MEAS) of all the gas sensors, the locations (LOCS) of all of the gas sensors, and the wind speed and direction (WIND) from the stochastic wind model. The general purpose of this step is to localize the leak source within some distance of the known leak source (e.g., using the same plume model data), noting that noise may be added to enhance robustness of the analysis in some embodiments. The predicted SOURCE of each test case is suitably stored (e.g., in the source identification store 98 discussed above) for later evaluation, as well as the amount of time (e.g., number of time intervals or time periods, number of simulated valid event records from the measurement profiles) utilized to predict the SOURCE for each test case.

For the embodiment illustrated in FIG. 12, the GGEA system 16 subsequently evaluates (block 212) the simulated performance of the gas sensors at the defined locations based on the stored predicted SOURCE of each test case and/or the time involved determining in each SOURCE prediction. For example, in some embodiments, the gas sensor arrangement may be evaluated based on the amount of time utilized to predict the SOURCE of each of the test cases, wherein a lower or minimized time is desirable. In some embodiments, the gas sensor arrangement may be additionally or alternatively evaluated based on a distance or difference between each predicted location of the gas leak and the actual location of the gas leak as defined by each test case, wherein a lower or minimized distance is desirable. It may be appreciated that other metrics may also be used, in accordance with the present disclosure.

For example, in certain embodiments, the total time (T) to resolve all test cases may be given by Equation 4:

$$T = \sum_{i=1}^{n_d} t_i^{min} \qquad \text{Equation 4}$$

wherein $t_i^{min}$ is the minimum time to predict the SOURCE for each test case (e.g., product of the number of time periods from which MEAS data is used and the time period duration), and $n_d$ is the total number of test cases in the test schedule. For example, in some embodiments, $t_i^{min}$ may be calculated as the product of the number of time periods (from which MEAS data of the gas sensors and WIND data is utilized to predict the SOURCE to a predefined level of accuracy) and the time period duration. It may be appreciated that a similar calculation may be performed to calculate a total difference in distance between the predicted and defined source locations across all test cases. In the above example, the number of sensors n with locations LOCS give rise to some measure of time taken to resolve all possible leak cases listed in the test schedule. In some embodiments, a cost measure might be stipulated that accounts for the number of gas sensors used and the total time (or distance or other metric) taken to identify the gas leaks, plus penalties for gas leaks which go undetected (e.g., using a long-time result and a non-detection penalty). In embodiments, a cumulative value representative of all tests (e.g., V(LOCS)) may be generated, which is the solution to an optimization problem that identifies the optimal location of the gas sensors in LOCS. Thus, the optimal gas sensor arrangement can be determined for a given number of sensors n. As indicated by the arrow 214, the number of locations of the gas sensors may be modified at block 198 (e.g., incrementing the number of gas sensors), and the remainder of the process 190 repeated to evaluate the new gas sensor arrangement. For example, in some embodiments, the arrangement with the least cost that detects the highest number of gas leaks in the test schedule in the least time provides the optimal number of gas sensors, as well as their optimal locations within the worksite.

Thus, in certain embodiments of the disclosure, a gas leak identification is enabled when gas concentration measurements are available from a defined number of gas sensors at defined locations within the domain of interest. Certain embodiments enable the determination of the optimal number of gas sensors and their placement in a predictive approach. In certain embodiments of the disclosure, the disclosed technique accounts for the human operator input that led to manual placement of the gas sensors, a trial-and-error approach, or a random placement of the gas sensors in the vicinity of components likely to leak.

In certain embodiments of the disclosure, prior information may be assumed from a list of known components and their locations. In certain embodiments, the probability of a gas leak might also be included to prioritize the selection of those sites before others. However, if there is only one gas leak, the leaking component should be identified in any case. Further, the probability of leak may also be used to filter the set of possible locations or sub-domains, enabling leak source identification to be performed based on leak probability groups. In certain embodiments, this leak probability information may be included (e.g., as discrete point-locations) as part of a constraint. In embodiments of the disclosure, components of the worksite may be ranked for likelihood of leak based on past human operator data or insight, and these components may be grouped by probability and solved in turn. This means that for each sub-problem, the most likely leak components/location will be solved first before moving to the next probability group of worksite components. If only one leak is anticipated, this one occurrence may be identified as the source of the leak over all other items in the set (e.g., by testing each leak scenario).

It is also possible that certain locations (e.g., certain regions of interest) may naturally present high levels of methane concentration. For example, this could be due to proximity to farms, life-stock, marshland, or other naturally occurring sources. In this regard, in embodiments of the disclosure, a background level may be established by measuring the methane concentrations at all gas sensors of the worksite prior to performing leak source localization. Using the gas concentration measurements collected when no leaks are present, or data at gas sensors positioned opposite to the wind direction with respect to an expected leak, enables determination of the ambient background concentrations of the gas. In some embodiments, ambient background concentration is used to offset the gas concentration measurements of each gas sensor.

In embodiments of the disclosure, real-time acquisition of data from gas sensors is provided. In some embodiments, the possibility of noise may result in the gas concentration measurement or signal being smoothed and/or averaged. However, the use of average measurements (in place of disclosed valid event records) may be less effective in the source identification process. The valid event records of the event record store may include some averaging, as discussed above with respect to FIGS. 5 and 6. For example, zero or low-level null gas concentration readings may be averaged to indicate the ambient level at each gas sensor.

In embodiments of the disclosure, the GGEA system 16 may also account for seasonal factors. As noted, when determining the optimal gas sensor arrangement, a stochastic wind model representative of the prevailing conditions on a given site over a given period of interest may be used. Notably, it is recognized that the wind behavior may change with season. As such, in some embodiments, the forecast period of interest may be extended to include this variability, or the prediction model could be performed over a number of wind models to account for seasonal change. In this manner, the determination of the optimal gas sensor arrangement may then include the effects of seasonal variability. Additionally, to address seasonality and better understand the most likely conditions on a given worksite, embodiments of the disclosure may account for or utilize historical data (e.g., weather, rainfall, wind, solar, temperature, etc.) from any suitable public and private sources. This information can be used to inform the wind models in the determination of the optimal gas sensor arrangement. In some embodiments, real-time weather data may be used to validate the on-site wind measurements, and used in place of on-site wind measurements when wind sensors are not available or not working at the worksite.

In certain embodiments, the disclosed techniques may be applied subject to uncertainty in the gas or wind measurements or the parameters in the forward model. For example, this may entail sampling over the uncertainty space of each uncertain parameter and optimizing the residual mis-match function, like discussed above, except it may be performed according to a user-defined confidence factor, such as discussed in *Handbook of Metaheuristics*, Michel Gendreau and Jean-Yves Potvin, Eds., Springer, 2019. The variability associated with wind conditions may naturally present a distribution of possible source locations that can be shown graphically on the facility map. In the absence of model uncertainty and measurement noise for both of gas sensors and wind meters, disclosed techniques permit leak source identification with greater certainty.

The specific embodiments described above have been illustrated by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

In the claims, means-plus-function clauses are intended to cover the structures described herein as performing the recited function and not only structural equivalents, but also equivalent structures. Thus, for example, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

The invention claimed is:

1. A greenhouse gas emission analysis (GGEA) system, comprising:
    at least one memory configured to store a plume model; and
    at least one processor configured to execute stored instructions to perform actions comprising:
        receiving gas concentration measurements from gas sensors communicatively coupled to the GGEA system;
        receiving wind measurements from wind sensors communicatively coupled to the GGEA system;
        convolving the gas concentration measurements and the wind measurements into valid event records; and
        predicting a location and leak rate of a gas leak within a worksite based at least in part on the valid event records and the plume model, comprising, for each potential gas leak location and each potential gas leak rate:
            summing, for each gas sensor of the gas sensors, a cost function value that compares a gas concentration measurement of the gas sensor from a valid event record with a gas concentration predicted for the gas sensor by the plume model using, as input, at least the potential gas leak location, the potential gas leak rate, a location of the gas sensor, and wind measurements of the valid event record; and
            selecting the potential gas leak location and the potential gas leak rate that yields a lowest summed cost function value as the predicted location and leak rate of the gas leak.

2. The GGEA system of claim 1, wherein the plume model is also configured to receive, as input, an initial plume jet momentum and direction, a composition and/or density of a leaking gas, a detailed two dimensional (2D) or three-dimensional (3D) worksite plan, an aerial or satellite view of the worksite, atmospheric information, vertical wind profiles, solar radiation intensity, vertical temperature profiles, humidity, cloud cover, presence of inversion layers, atmospheric stability classes, or combinations thereof.

3. The GGEA system of claim 1, wherein, to convolve the gas concentration measurements and the wind measurements into the valid event records, the at least one processor is configured to execute stored instructions to perform the actions comprising:
    synchronizing the gas concentration measurements and the wind measurements based on a time at which the gas concentration measurements and the wind measurements were collected.

4. The GGEA system of claim 1, wherein the gas sensors comprise at least one optical gas imaging (OGI) sensor.

5. The GGEA system of claim 1, wherein the wind measurements comprise at least wind direction, wind speed, and wind variability over time.

6. The GGEA system of claim 1, wherein the at least one processor is configured to execute stored instructions to perform the actions comprising:
    receiving meteorological data from a communicatively coupled external weather service; and
    convolving the gas concentration measurements, the wind measurements, and the meteorological data into the valid event records,
    wherein at least a portion of the wind measurements are received from the communicatively coupled external weather service.

7. The GGEA system of claim 1, wherein the at least one processor is configured to execute stored instructions to perform the actions comprising:
    storing the valid event records in an event record store in the at least one memory.

8. The GGEA system of claim 1, wherein the gas leak is a methane gas leak.

9. The GGEA system of claim 1, wherein the gas sensors, the wind sensors, and the gas leak are disposed within an oil and gas worksite.

10. The GGEA system of claim 1, wherein the plume model is a Gaussian plume dispersion model, a plume model based on computational fluid dynamics (CFD), a plume model based on trained machine learning models, or a plume model for flow around structures.

11. The GGEA system of claim 1, wherein the GGEA system is implemented as an edge device in a cloud-based computing environment.

12. A method of predicting a location and leak rate of a gas leak within a worksite, the method comprising:
    receiving gas concentration measurements from gas sensors disposed within the worksite;
    receiving wind measurements from wind sensors disposed within the worksite;
    convolving the gas concentration measurements and the wind measurements into valid event records; and
    predicting a location and leak rate of a gas leak within the worksite based at least in part on the valid event records and a plume model, comprising, for each potential gas leak location and each potential gas leak rate;
        summing, for each gas sensor of the gas sensors, a cost function value that compares a gas concentration measurement of the gas sensor from a valid event record with a gas concentration predicted for the gas sensor by the plume model using, as input, at least the potential gas leak location, the potential gas leak rate, a location of the gas sensor, and wind measurements of the valid event record; and
        selecting the potential gas leak location and the potential gas leak rate that yields a lowest summed cost function value as the predicted location and leak rate of the gas leak.

13. The method of claim 12, wherein convolving the gas concentration measurements and the wind measurements into the valid event records comprises:
    synchronizing the gas concentration measurements and the wind measurements based on a time at which the gas concentration measurements and the wind measurements were collected; and
    performing data smoothing of the synchronized gas concentration and wind measurements.

* * * * *